United States Patent [19]
Karell

[11] Patent Number: 5,334,212
[45] Date of Patent: Aug. 2, 1994

[54] EAR WAX EXTRACTOR WITH DEPTH CONTROL

[76] Inventor: Manuel L. Karell, 3573 - 22 St., San Francisco, Calif. 94114

[21] Appl. No.: 153,880

[22] Filed: Nov. 17, 1993

[51] Int. Cl.$^5$ ............................................. A61F 11/00
[52] U.S. Cl. ........................... 606/162; 606/172; 606/160; 128/864
[58] Field of Search ............................ 128/864–868; 606/160, 162, 172

[56] References Cited

U.S. PATENT DOCUMENTS

| | | | |
|---|---|---|---|
| 92,980 | 7/1869 | Lovell | 606/162 |
| 102,351 | 4/1870 | Wood | 606/162 |
| 147,660 | 2/1874 | Leiner | 606/162 |
| 320,889 | 6/1885 | Ruoff | 606/162 |
| 1,450,612 | 4/1923 | Schultz | 606/160 |
| 3,099,263 | 7/1963 | Palazzolo | 606/162 |
| 3,203,418 | 8/1965 | Johnston | 606/162 |
| 3,626,946 | 12/1971 | Messey | 606/162 |
| 4,411,265 | 10/1983 | Eichenlaub | 128/864 |
| 5,107,861 | 4/1992 | Narboni | 128/864 |
| 5,183,461 | 2/1993 | Hobbs | 606/162 |
| 5,209,757 | 5/1993 | Krug et al. | 606/162 |
| 5,234,452 | 10/1993 | Wang-On | 606/160 |

*Primary Examiner*—Robert A. Hafer
*Assistant Examiner*—Michael O'Neill

[57] ABSTRACT

The Humble Wax Remover TM —a safe ear wax extractor is composed of two parts; a safety stopper (10) and a loop curette wax extractor (26), whereby the second part is inserted into the first part thereby making a functional unit. The entire unit is then placed into the ear canal (FIG. 4). Once the unit is inserted into the canal, the handle (20) is rotated, wax is caught in the loop and then the unit is extracted from the canal. Wax is thereby safely extracted from the ear canal. Reinsertion is done until all wax is extracted. Readjustment of depth of insertion is accomplished by changing position of safety stopper with the loop curette wax extractor. Wax is thereby extracted without visualization of ear drums and thereby can be accomplished by lay persons.

1 Claim, 3 Drawing Sheets top side

EAR WAX EXTRACTOR WITH DEPTH CONTROL

BACKGROUND—FIELD OF INVENTION

The HUMBLE WAX REMOVER TM —safe ear wax extractor, generally relates to medical apparatus, and more particularly to a novel apparatus inserted into the ear for the safe removal of ear wax.

BACKGROUND—DESCRIPTION OF PRIOR ART

Ear wax accumulation prevents good hearing and prevents proper hearing aid functioning. Ear wax also prevents good visualization of the ear drums by health professionals. Various methods have been used to extract the wax, for example, U.S. Pat. No. 5,107,861 to Narboni, 1992, which uses a ear wax clean button and tubular wax collector inserted into the ear. Another apparatus, U.S. Pat. No. 4,411,265 to Eichenlaub, 1979, uses a fluid filled curette to irrigate wax out of the ear. Some physicians use a Water Pik TM dental cleaning device or a syringe to irrigate the ear and float the wax out of the canal. A specially designed ear curette with a wire loop is also used by physicians to manually extract the wax; however, the ear drum has been inadvertently injured in its use.

SUMMARY

The Humble Wax Remover TM —a safe ear wax extractor is composed of two pans: a safety insertion depth stopper mechanism and a loop curette wax extractor, whereby the second pan is inserted into the first part thereby making a functional unit. The unit is then placed into the ear canal. The stopper mechanism is held tightly against the outer ear, the handle is rotated, wax is caught in the loop and then the unit is extracted from the canal. Wax is thereby safely extracted from the ear canal. Reinsertion is done until all wax is extracted. Readjustment of depth of insertion is accomplished by changing position of safety insertion depth stopper with the loop curette wax extractor.

The Humble Wax Remover TM —a safe ear wax extractor enables the safe extraction of the wax without visualization of the canal or ear drum. It enables lay persons to extract wax from their own ears or from their children's ears.

BRIEF DESCRIPTION OF DRAWINGS

FIGS. 5, 5A, and 5B shows a plan view of an alternative embodiment showing fixed differing position stopper on curette with handle.

DETAILED DESCRIPTION OF THE PREFERRED EMBODIMENT

Figure 1:
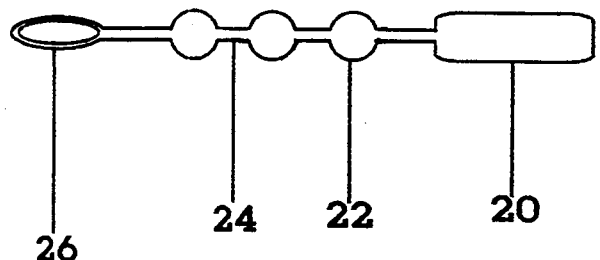
FIG. 1 is a plano drawing of the loop curette wax extractor of the Humble Wax Remover TM 13 a safe ear wax extractor.
Figure 2:
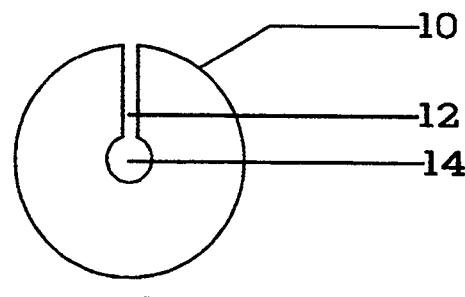
FIGS. 2 and 2A are plano drawings of the insertion depth stopper mechanism of the Humble Wax Remover TM —a safe ear wax extractor.
Figure 2A:
Figure 3:
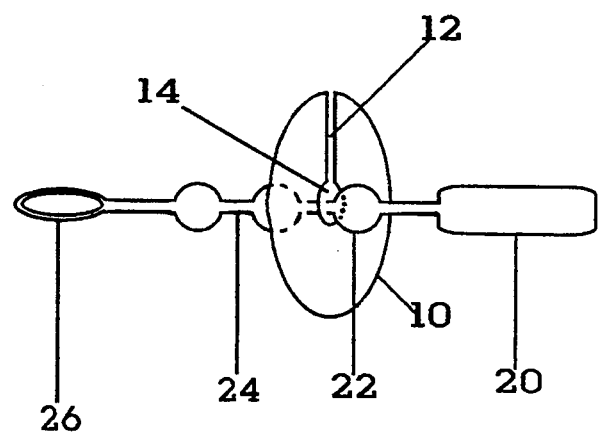
FIG. 3 is a plano view of the functional unit comprising the insertion depth stopper and loop curette extractor in operational mode.
Figure 4:
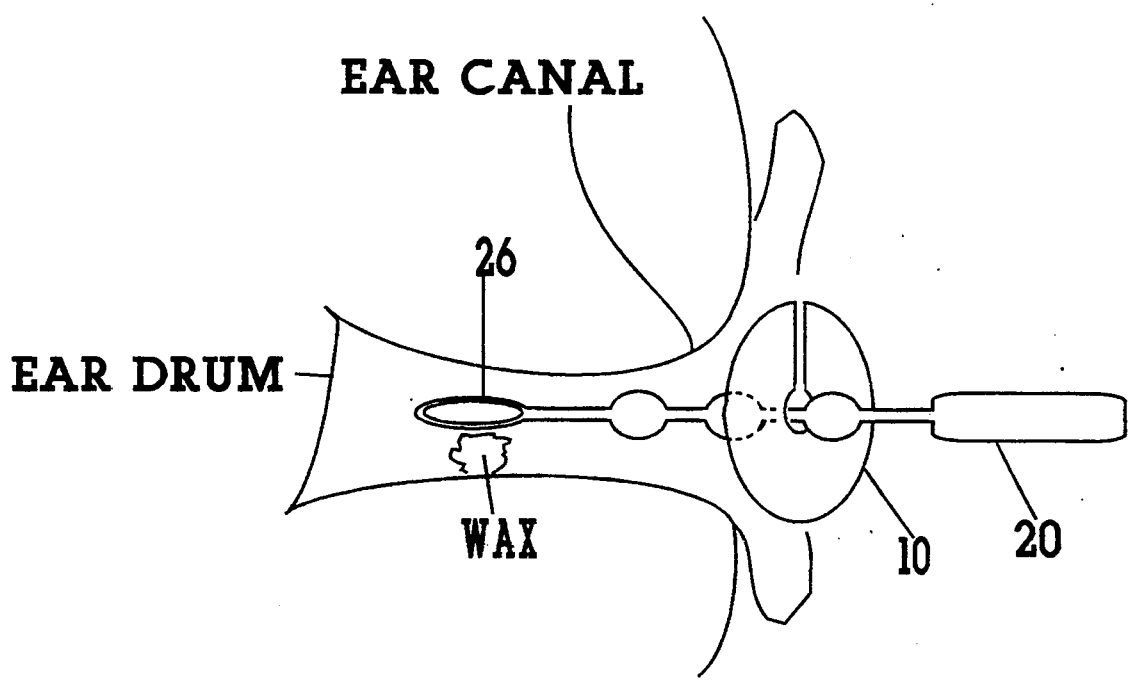
FIG. 4 shows a schematic representation of the Humble Wax Remover TM —a safe ear wax extractor in a human ear canal.

The Humble Wax Remover TM —a safe ear wax extractor comprises two separate components (FIG. 1 and FIG. 2), one component which fits into the other thereby making a functional unit (FIG. 3 ). FIG. 2 shows a body of an insertion depth stopper mechanism comprising a solid body (10), with a slit (12), ending in a centrally placed widened hole (14). FIG. 1 shows a loop curette apparatus having a handle (20) at one end, a loop curette (26) at the other end, with interconnectors (24) and bead-like protrusions (22) between handle (20) and loop curette (26). FIG. 3 shows the two separate parts joined together to make a functional unit, in which it can be seen that interconnectors (24) rest in central hole (14) of body (10). The apparatus is made of extruded plastic components, such as polypropylene, whereby the interconnectors (24) are sufficiently wide and the central slit (12) sufficiently narrow to prevent the loop curette (26) from slipping during handle (20) rotation. FIG. 4 shows the unit placed into a schematic representation of a human ear.

Figure 5:
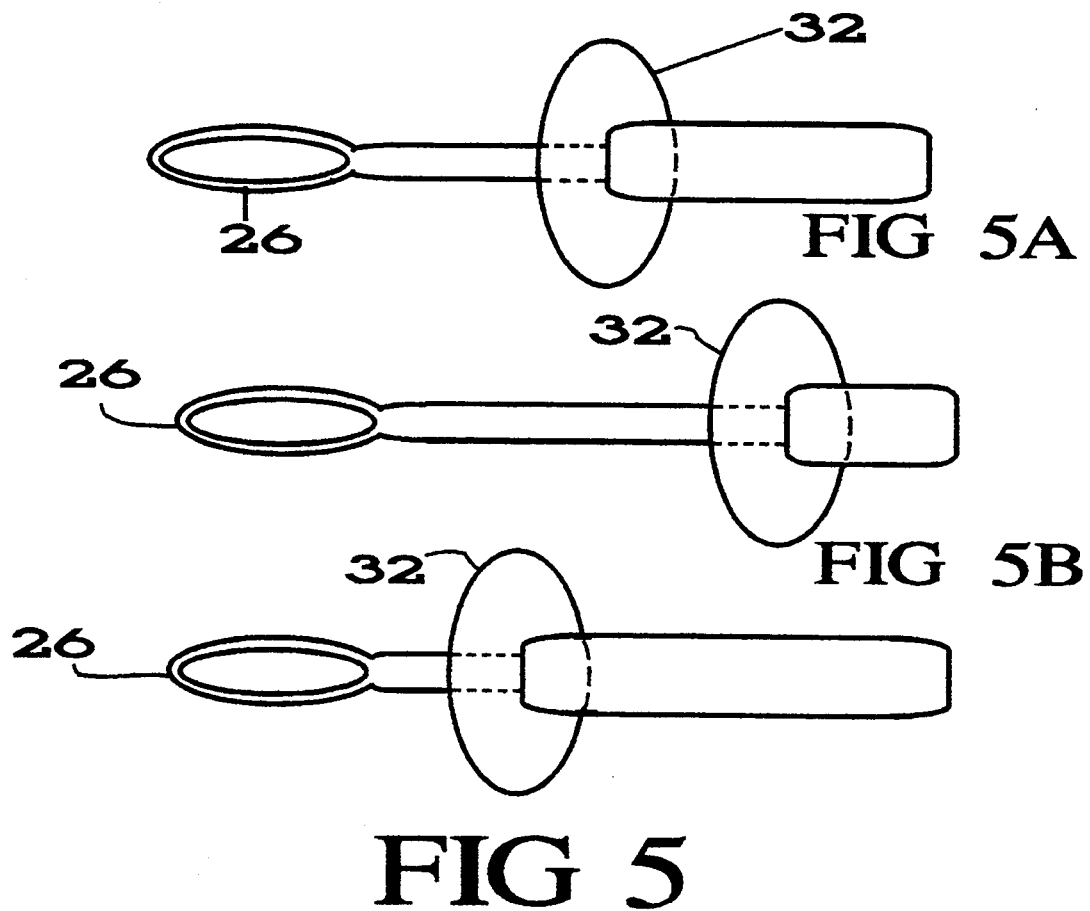
Figure 6:
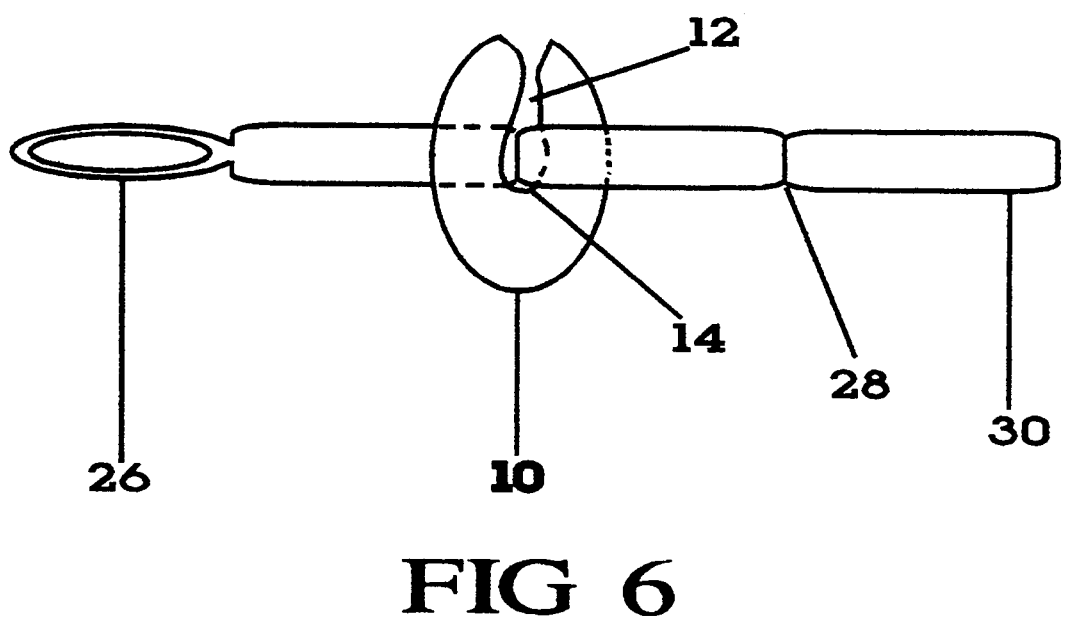
FIG. 6 shows a plano view of alternative embodiment.

An alternative embodiment shown in FIG. 5 would be a permanently attached stopper mechanism (32), placed in different locations for differing sized ear canal lengths. A still further embodiment shown in FIG. 6 would be a loop curette (26) having a long handle (30) which has scored indentations (28) allowing for stopper mechanism adjustment.

I claim:

1. An apparatus adapted to remove wax from the ear comprising:

a means to extract wax, a means to control the depth of insertion of said means to extract wax, and a means to adjust the depth of said means to extract wax;

wherein said means to extract wax is a loop curette, said curette having a shaft with a loop at one end, a handle for rotation at the other end and in between spacer bead-like protrusions;

wherein said means to control the depth of insertion of said loop curette is a stopper having a slit and central resting hole:

whereby said stopper surrounds said shaft and held in place adjacent bead-like protrusions;

whereby, said loop curette and said stopper will act as a functional unit when inserted into the ear canal, preventing the loop curette from being inserted too far into the ear canal, thereby preventing ear drum injury as the wax is removed.

* * * * *